(12) United States Patent
Marshall et al.

(10) Patent No.: US 6,932,793 B1
(45) Date of Patent: Aug. 23, 2005

(54) MEDICAL INJECTION DEVICES

(75) Inventors: Jeremy Marshall, Oxford (GB); Glenn Davison, Oxon (GB)

(73) Assignee: Owen Mumford Limited, Oxford (GB)

( * ) Notice: Subject to any disclaimer, the term of this patent is extended or adjusted under 35 U.S.C. 154(b) by 0 days.

(21) Appl. No.: 09/622,159

(22) PCT Filed: Feb. 15, 1999

(86) PCT No.: PCT/GB99/00473

§ 371 (c)(1),
(2), (4) Date: Sep. 25, 2000

(87) PCT Pub. No.: WO99/40958

PCT Pub. Date: Aug. 19, 1999

(30) Foreign Application Priority Data

Feb. 14, 1998 (GB) .................................. 9803084

(51) Int. Cl.⁷ ............................................ A61M 37/00
(52) U.S. Cl. ...................................... 604/135; 604/232
(58) Field of Search ........................ 604/131, 134–136, 604/156, 157, 187, 209–211, 68, 71, 232

(56) References Cited

U.S. PATENT DOCUMENTS 5,092,842 A    3/1992  Bechtold et al.
5,300,030 A *  4/1994  Crossman et al. .......... 604/136
5,599,309 A *  2/1997  Marshall et al. ............ 604/136
5,637,094 A    6/1997  Stewart, Jr. et al.
5,779,677 A *  7/1998  Frezza ........................ 604/134
5,957,897 A *  9/1999  Jeffrey ........................ 604/223
6,099,503 A *  8/2000  Stradella .................... 604/135
6,159,181 A * 12/2000  Crossman et al. .......... 604/157

FOREIGN PATENT DOCUMENTS

WO    WO 8808725    11/1988
WO    WO 9421316     9/1994
WO    WO 9940958     8/1999

* cited by examiner

*Primary Examiner*—Justine R. Yu
*Assistant Examiner*—Huyen Le
(74) *Attorney, Agent, or Firm*—Young & Thompson

(57) ABSTRACT

A firing device has a housing (10, 20) for an injector (1) with a trigger (4) whose action to eject a dose from its needle (2) is forwards against a resistance. The housing contains a spring (24) which acts on an axially movable locator (23) for the injector (1) that co-operates with its trigger (4). The device is primed by compressing the spring (24), the injector then being latched in a rearward position. Release of the catch (28) causes the spring (24) first to propel the injector (1) forwards, acting through the locator (23) and trigger (4), until the needle (2) is projected, and then to overcome the resistance to the trigger (4) to actuate that and cause a dose to be ejected.

7 Claims, 3 Drawing Sheets

MEDICAL INJECTION DEVICES

Figure 1:
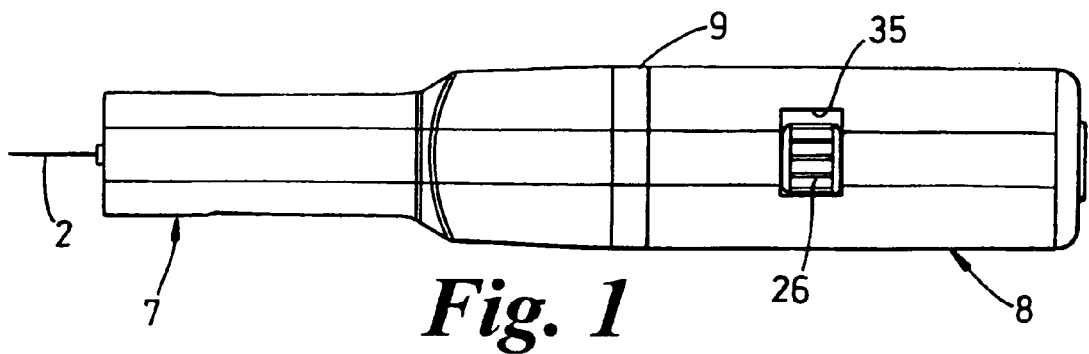

This invention relates to medical injection devices. It is particularly concerned with the automatic firing of an injector having a barrel-like body with a sliding trigger on one side to eject the dose from a needle at its forward end. The action of the trigger is forwards against a stiff spring. Preferably, there is a dose setting mechanism such as a rotary knob at its rear end which may be "clicked" round to a desired setting. All the trigger does is to release a spring which shoots a plunger forwards by an amount determined by the knob, this plunger co-operating with a piston in a capsule carrying the dose.

Such injectors are well known, but they require the user to insert the needle into the flesh first, before releasing the trigger. For self-users, this can be particularly difficult: it is natural to flinch and not push the needle in far enough.

The aim of this invention is to provide a device that can automate this operation, ensuring that the injector needle is thrust in to the correct degree before the dose is ejected.

According to the present invention there is provided a a firing device for an injector having a barrel-like body with a sliding trigger on one side to eject the dose from a needle at its forward end, the action of the trigger being forwards against a resistance, the device comprising a generally cylindrical housing for the injector, a forward portion of the housing, open at its forward end for projection of the injector needle, containing spring means for exerting a light rearward force on the injector, and a rearward portion of the housing having an axially movable, forward spring-loaded member to cooperate with the injector trigger, an external cocking mechanism operable to energise the spring loading of said member, and an operating element to release that loading to cause the member first, acting through the injector trigger, to shoot the injector forward against the light rearward force of said spring means to a needle projecting position, and then to overcome said resistance operate the trigger to eject the dose from the injector.

The spring-loaded member may be generally tubular to embrace the injector, a coil spring acting between its rear end and an internal abutment at the rear end of the barrel.

Conveniently, an axial slot, open from the forward end of the tubular member, receives the trigger and thereby locates the injector rotationally. The trigger will be engaged by the closed rear end of this slot.

The cocking mechanism is preferably a sleeve over the rearward portion of the housing with at least one lateral projection from the tubular member projecting through an axially parallel slot in the housing into an axially parallel slot in the sleeve, the cocking action being to pull the sleeve rearwardly so that the projection engaged by the forward end of its slot takes the tubular member with it until there is snap engagement between the tubular member and the barrel, the injector being pushed back at the same time by the spring means.

This arrangement also ensure that there is no mutual rotation between the tubular member, the housing and the sleeve.

Conveniently, the sleeve carries the operating element which can only register in a position to release the snap engagement when the sleeve is moved forwards again after the device has been cocked. The operating element is preferably a button which engages in a slot in the housing and which has two different positions between which it can be shifted circumferentially of the sleeve only when that is forwards. In one said position it acts by co-operation with a step in the slot as a preventer against the sleeve being slid rearwardly, that position also being the one, when the sleeve is moved forwards after cocking, in which the device can be fired. In the other said position, it allows the external sleeve to be slid rearwardly (and forwardly again) but is ineffective, when pressed, to fire the device.

When the device is for an injector having a rear end rotary adjusting knob to set the amount of dose to be ejected, the sleeve, in its forward position with the device cocked, conveniently leaves this knob exposed whereby, before firing, the user can rotate the knob to the required dosage. Marks on the knob may register with a mark on the end of the sleeve to assist gauging the amount of dosage set.

Figure 2:
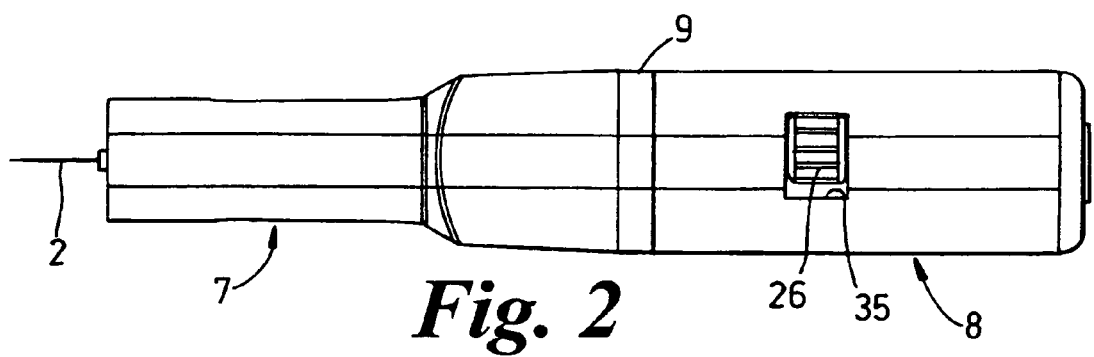
Figure 6:
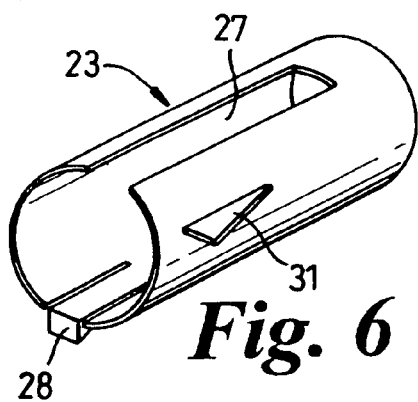
Figure 7:
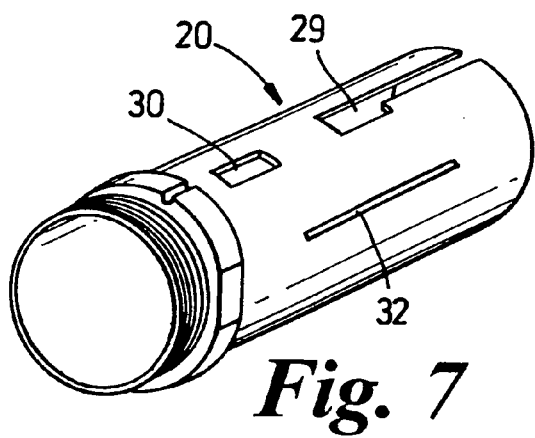
Figure 8:
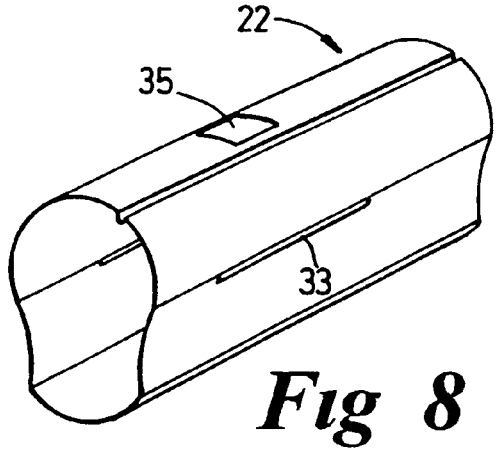
Figure 3:
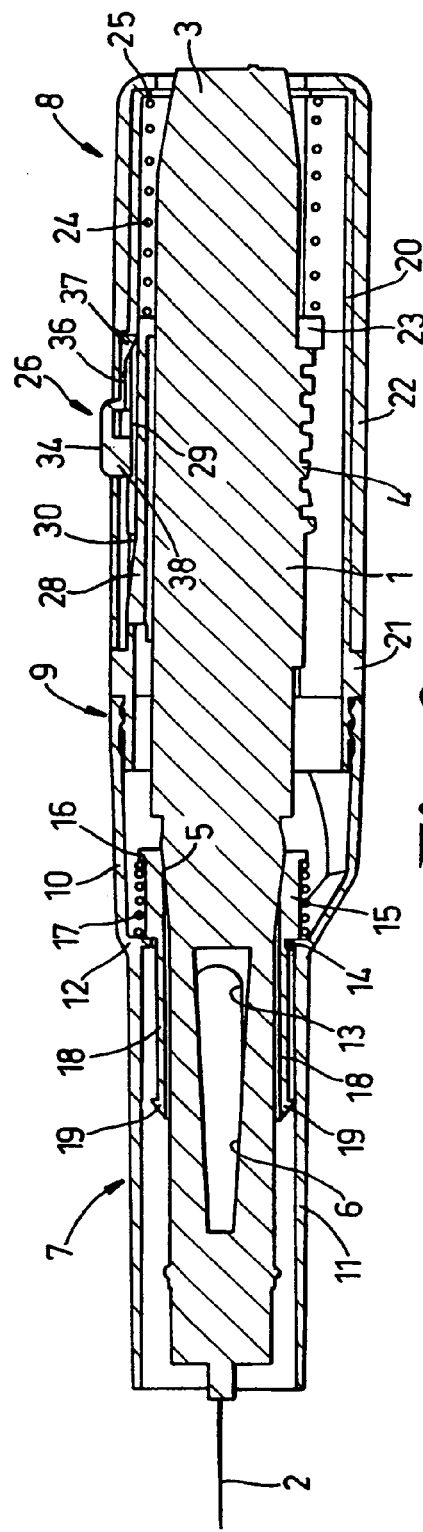
Figure 4:
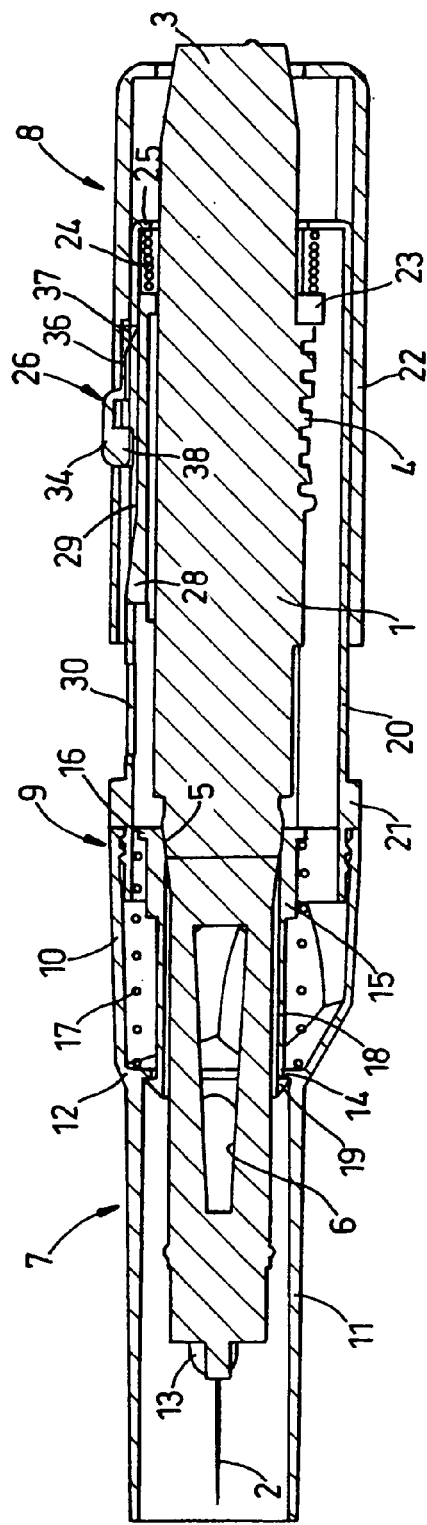
Figure 5:
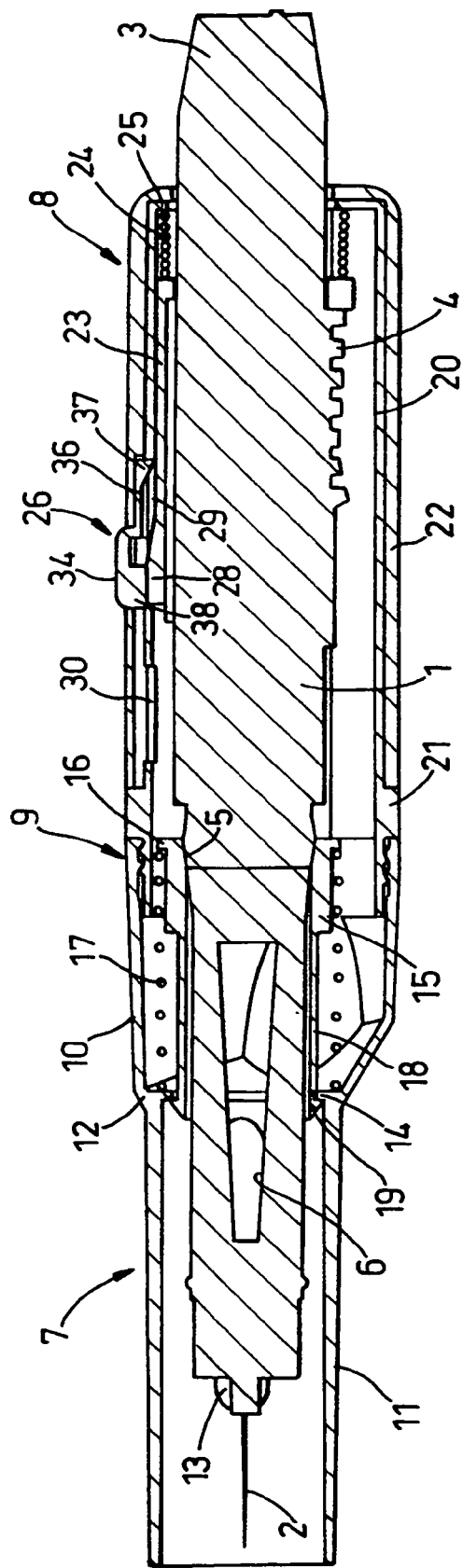

For a better understanding of the invention one embodiment will now be described, by way of example, with reference to the accompanying drawings, in which:

FIG. 1 is a side view of a firing device for an injector with a firing button in a locked and firing position, FIG. 2 is a similar side view but with the firing button in a cocked position, FIG. 3 is an axial section of the device, charged with an injector, in an idle position, FIG. 4 is a similar axial section with the device just cocked, FIG. 5 is a similar axial section with the device cocked and ready to fire, FIG. 6 is a perspective view of a locator tube forming part of the device, FIG. 7 is a perspective view of a barrel into which the locator tube fits, and FIG. 8 is a perspective view of a sleeve into which the barrel fits.

The injector 1 to be fired is of known type and will not be described in detail. But its salient features for the purposes of this specification are a needle 2 at its forward end, a rotatable knob 3 at its rear end which is "clicked" round to set the desired dosage, and an elongate trigger 4 on the side of the barrel-like body towards the rear end whose firing action is forwards against a stiff spring or some other resistance. The body of the injector narrows at a sloping shoulder 5 towards a forward end portion which has opposed windows 6 through which the capsule containing the medium to be injected can be seen.

The firing mechanism into which this injector fits has two assemblies 7 and 8 which screw together at 9. The nose assembly 7 consists of a stepped tube 10 with a cylindrical portion 11 forward of a shoulder 12 provided with opposed windows 13 which will register with the windows 6. Internally at the shoulder 12 there is an annular rib 14 which limits the fore and aft travel of a locator ring 15. This has an outwardly projecting rib 16 at its rear end, and a spring 17 acts between that rib and the root of the rib 14 to urge the locator ring 15 rearwardly with a fairly light force. Two diametrically opposed arms 18 project forwardly from the ring 15 and hooks 19 at their ends can snap past the rib 14 on assembly. The travel of the locator ring is determined by the length of these arms 18 to the hooks 19. The locator ring 15 has guide means (not shown) to keep it from rotating while allowing axial movement, and the gaps between the arms 18 register with the windows 13.

The rear assembly 8 consists of a barrel 20, with a wide external annular rib 21 just to the rear of the screw thread joint 9, a sleeve 22 encasing the barrel 20 to the rear of the rib 21, a generally tubular locator 23 for the injector within the barrel urged forwardly by a powerful spring 24 reacting against an inturned flange 25 at the rear end of the barrel, and a trigger 26 captive to the sleeve 22. The tube 10 and barrel 20, screwed together, form a housing.

The locator 23 (FIG. 6) has a wide slot 27 extending lengthways, open at its forward end and with a blind rear end, to accommodate the injector trigger 4. Diametrically opposite this a tongue 28 is integrally formed with the tube at its forward end, the free end of the tongue being thickened to project proud of the otherwise cylindrical envelope. The barrel 20 (FIG. 7) has a slot 29 and an aperture 30 with which this tongue 28 can engage. The slot 29 is L-shaped in profile, open to the rear end of the barrel and with its short leg forward and aligned axially with the aperture 30. When the tongue 28 is latched into the slot 29, engaging its forward end, it holds the locator 23 back against the compressed spring 24, and when released from that it snaps into the aperture 30 to assist termination of the forward motion of the locator 23.

The locator 23 also has two diametrically opposed fins 31 which project through longitudinal slots 32 in the barrel 20, the leading edges of these fins being radial but the rear edges having a shallow slope so that the tube is radially contracted by a wedging action as it is forced rearwardly into the barrel on assembly. The slot 27 makes this deformation possible. When the fins 31 reach the slots 32 they spring outwards making the locator 23 captive to the barrel 20. Furthermore, their tips are then proud of the barrel and the sleeve 22 (FIG. 8) has longitudinal slots 33 in which those tips can engage in like manner, making the sleeve captive also. The leading ends of the slots 33 serve as stops in a manner described below. The fins 31 also ensure that there is no mutual rotation between the locator 23, the barrel 20 and the sleeve 22.

A single fin might suffice, but two are preferred.

The trigger 26 has an exposed button 34 projecting through the slot 29, in which it is captive, and through an aperture 35 in the sleeve 22. This aperture allows the button to be shifted circumferentially between the positions shown in FIGS. 1 and 2 when it registers with the wide, forward end of the slot 29. The trigger is retained by a plate-like extension 36 from its base which engages under the periphery of the aperture 35 and which at its rear end has an inwardly projecting wedge-shaped stud 37. Below the front of the button there is a thickened portion 38 to co-operate with the tongue 28.

The rear ends of the barrel 20, the sleeve 22 and the locator 23 are open so that the injector 1 can be fitted as shown in FIG. 3, the rear end of its trigger 4 bearing against the closed end of the slot 27 and its dose adjusting knob 3 just exposed at the rear end of the injector. The sleeve 22 will have a mark against which rotation of the knob 3 can be gauged; the mark on the injector itself being hidden inside the assembly 8. With the injector so in place, the nose assembly 7 is screwed on, the locator ring engaging the sloping shoulder 5 of the injector and being forced forwardly in relation to the tube 10 against the spring 17. When assembly is complete, the forward end of the ring 15 bears against the rib 14 with the spring 17 compressed. But that spring is not nearly powerful enough to overcome the spring 24 and the locator 23 remains in the forward position with the tongue 28 in the aperture 30.

The needle 2 is left exposed projecting forward of the nose assembly 7. In practice, it will have a protective sheath while this fitting together is carried out, and it will not be removed until just before use.

In the FIGS. 1 and 3 position of the trigger 26 the stud 37 is captive in the slot 29, preventing the sleeve 22 from moving rearwardly. The device is in an idle or non-ready condition.

For use, the trigger 26 is pushed circumferentially to the FIG. 2 position to take the stud 37 out of engagement with the step formed by the short leg of the L-shaped slot 29. This trigger movement also takes the thickened portion 38 out of axial alignment with the tongue 28. The sleeve 22 can then be pulled back and, acting through the forward ends of its slots 33 and the fins 31, this also retracts the locator 23, compressing the spring 24. When fully retracted, the tongue 28 snaps into the slot 29, latching the device in the position of FIG. 4. During this operation the injector 1 is pushed back by the spring 17 acting through the locator ring 15 and the needle 2 is withdrawn into the tube 10.

The sleeve 22 is now slid forwards again to abut the rib 21, fully exposing the knob 3, which is rotated to set the required dose. The trigger 26 is pushed back circumferentially to the FIG. 1 position so that the stud 37 re-enters the short leg of the slot 29 while the portion 38 comes directly over the free end of the tongue 28. In this position of FIG. 5 the device is ready to fire.

The free end of nose portion 11 is held against the area of skin where the injection is to be made and the button 34 pressed. This releases the tongue 28 from the slot 29 and the spring 24 shoots the locator 23 forwards. The closed end of the slot 27 bearing on the trigger 4 carries the injector forwards as well, causing the needle 2 to penetrate the skin. The trigger 4 is not immediately activated, being held rearwardly by a spring or other resistance stiffer than the spring 17. But when the locator ring 15 meets the rib 12, the trigger 4 will be pressed forward sufficiently to trip the action of the injector. The dose is therefore ejected as the forward travel of the injector is completed, back to the FIG. 3 condition. The knob 3 returns to its zero position during this ejection.

The cycle is then ready to be repeated.

What is claimed is:

1. A firing device for use with an injector of the type having a barrel-like body enclosing a spring-loaded plunger to act on a piston within a capsule carrying a dose, and a sliding trigger on one side of the body actuable to release the plunger spring to drive the plunger to cause ejection of the dose from a needle at the forward end of the body, the action of the trigger being forwards against a resistance, the firing device comprising a generally cylindrical housing surrounding the injector, a forward portion of the housing, open at its forward end for projection of the injector needle, containing a locator spring for exerting a light rearward force on the injector to cause the needle to be located within said housing, and a rearward portion of the housing having an axially movable, forward spring-loaded actuating member to cooperate with the injector trigger, an external cocking mechanism operable to energize the spring loading of said actuating member with a spring force greater than said light rearward force, and an operating element to release that loading to cause the actuating member firstly, acting through the injector trigger, to shoot the injector forward against the light rearward force of said locator spring to a needle projecting position, and secondly to overcome said resistance in the injector and operate the injector trigger to cause ejection of the dose from the injector, said generally cylindrical housing being in two parts separably secured together in end-to-end relationship thereby releasably to contain a said injector, and wherein the spring-loaded member is generally tubular to embrace the injector, a coil spring acting between its rear end and an internal abutment at the rear end of the housing and wherein the cocking mechanism is a sleeve over the rearward portion of the housing with at least one lateral projection from the tubular member projecting through an axially parallel slot in the housing into an axially parallel slot in the sleeve, the cocking action being to pull the sleeve rearwardly so that the projection engaged by the forward end of its slot takes the tubular member with it until there is snap engagement between the tubular member and the barrel, the injector being pushed back at the same time by said spring means.

2. A firing device as claimed in claim 1, wherein an axial slot, open from the forward end of the tubular member, receives the trigger and thereby locates the injector rotationally.

3. A firing device for use with an injector of the type having a barrel-like body enclosing a spring-loaded plunger to act on a piston within a capsule carrying a dose, and a sliding trigger on one side of the body actuable to release the plunger spring to drive the plunger to cause ejection of the dose from a needle at the forward end of the body, the action of the trigger being forwards against a resistance, the firing device comprising a generally cylindrical housing surrounding the injector, a forward portion of the housing, open at its forward end for projection of the injector needle, containing a locator spring for exerting a light rearward force on the injector to cause the needle to be located within said housing, and a rearward portion of the housing having an axially movable, forward spring-loaded actuating member to cooperate with the injector trigger, an external cocking mechanism operable to energize the spring loading of said actuating member with a spring force greater than said light rearward force, and an operating element to release that loading to cause the actuating member firstly, acting through the injector trigger, to shoot the injector forward against the light rearward force of said locator spring to a needle projecting position, and secondly to overcome said resistance in the injector and operate the injector trigger to cause ejection of the dose from the injector, wherein the spring-loaded member is generally tubular to embrace the injector, a coil spring acting between its rear end and an internal abutment at the rear end of the housing, and the cocking mechanism is a sleeve over the rearward portion of the housing with at least one lateral projection from the tubular member projecting through an axially parallel slot in the housing into an axially parallel slot in the sleeve, the cocking action being to pull the sleeve rearwardly so that the projection engaged by the forward end of its slot takes the tubular member with it until there is snap engagement between the tubular member and the barrel, the injector being pushed back at the same time by said spring means.

4. A firing device as claimed in claim 3, wherein the sleeve carries the operating element which can only register in a position to release the snap engagement when the sleeve is moved forwards again after the device has been cocked.

5. A firing device as claimed in claim 4, wherein the operating element is a button which engages in a slot in the housing and which has two different positions between which it can be shifted circumferentially of the sleeve only when that is forwards, wherein in one said position it acts by co-operation with a step in the slot as a preventer against the sleeve being slid rearwardly, that position also being the one, when the sleeve is moved forwards after cocking, in which the device can be fired, and wherein in the other said position, it allows the external sleeve to be slid rearwardly (and forwardly again), but is ineffective, when pressed, to fire the device.

6. A firing device as claimed in claim 3, wherein the device is for an injector having a rear end rotary adjusting knob to set the amount of dose to be ejected, and wherein the sleeve, in its forward position with the device cocked, leaves this knob exposed whereby, before firing, the user can rotate the knob to the required dosage.

7. A firing device as claimed in claim 6, wherein marks on the knob register with a mark on the end of the sleeve to assist gauging the amount of dosage set.

* * * * *